US012758429B2

(12) United States Patent
Gross et al.

(10) Patent No.: US 12,758,429 B2
(45) Date of Patent: Oct. 13, 2026

(54) DEVICE FOR INTRODUCING A SEAL INTO AN EAR AND A METHOD FOR REPAIRING A TYMPANIC MEMBRANE

(71) Applicants: National University of Singapore, Singapore (SG); Hadasit Medical Research Services And Development Ltd, Jerusalem (IL); Yissum Research Development Company of the Hebrew University of Jerusalem Ltd, Jerusalem (IL)

(72) Inventors: Menachem Gross, Jerusalem (IL); Shlomo Magdassi, Jerusalem (IL); Yin Chiang Boey, Singapore (SG); Ngeow Khing Chia, Singapore (SG)

(73) Assignees: National University of Singapore, Singapore (SG); Hadasit Medical Research Services And Development Ltd, Jerusalem (IL); Yissym Research Development Company of the Hebrew University of Jerusalem, Ltd, Jerusalem (IL)

( * ) Notice: Subject to any disclaimer, the term of this patent is extended or adjusted under 35 U.S.C. 154(b) by 792 days.

(21) Appl. No.: 17/801,661

(22) PCT Filed: Mar. 11, 2021

(86) PCT No.: PCT/SG2021/050129

§ 371 (c)(1),
(2) Date: Aug. 23, 2022

(87) PCT Pub. No.: WO2021/183057

PCT Pub. Date: Sep. 16, 2021

(65) Prior Publication Data

US 2023/0157896 A1 May 25, 2023

Related U.S. Application Data

(60) Provisional application No. 62/988,590, filed on Mar. 12, 2020.

(51) Int. Cl.
*A61F 11/20* (2022.01)
*A61B 1/227* (2006.01)
*A61F 2/18* (2006.01)

(52) U.S. Cl.
CPC .............. *A61F 11/20* (2022.01); *A61B 1/227* (2013.01); *A61F 2/18* (2013.01); *A61F 2002/183* (2013.01)

(58) Field of Classification Search
CPC ... A61B 1/227; A61B 17/0218; A61B 1/2275; A61B 1/233; A61F 11/20
(Continued)

(56) References Cited

U.S. PATENT DOCUMENTS 5,916,150 A * 6/1999 Sillman .................. A61B 10/06 600/184
2007/0082052 A1 4/2007 Bonassar et al.
(Continued)

FOREIGN PATENT DOCUMENTS

DE 4400188 A1 * 7/1994 ......... A61B 17/0057
WO 1999011175 A1 3/1999
WO 2012120513 A1 9/2012

OTHER PUBLICATIONS

International Search Report for International Application No. PCT/SG2021/050129 mailed May 1, 2021, 4 pages.
(Continued)

*Primary Examiner* — Eduardo C Robert
*Assistant Examiner* — Tara Rose E Carter
(74) *Attorney, Agent, or Firm* — Botos Churchill IP Law LLP

(57) ABSTRACT

The present invention relates to a device for repair of a region within an ear via a natural orifice, the device com-
(Continued)

prising a body. The body comprises a first port for visibly identifying the region to be sealed, the region being inside the ear; and a second port through which a seal can be introduced into the ear through the device. The region comprises a perforation of a tympanic membrane of the ear and the device is a speculum. The present invention also relates to method for repairing a perforation in a tympanic membrane using the same device.

13 Claims, 4 Drawing Sheets

(58) Field of Classification Search
USPC .................................................. 600/201–245
See application file for complete search history.

(56) References Cited

U.S. PATENT DOCUMENTS

2008/0003205 A1* 1/2008 Bonassar ............ A61L 27/3804 424/488
2011/0166421 A1 7/2011 Katiraei
2011/0295073 A1* 12/2011 Truong .................. A61B 1/227 600/187
2012/0179187 A1* 7/2012 Loushin ............ A61B 10/0045 606/185
2013/0023914 A1* 1/2013 Truong .................. A61B 1/015 606/162
2015/0238180 A1* 8/2015 Weitzner ................ A61B 1/018 600/208
2017/0156853 A1* 6/2017 Weber ....................... A61F 2/18
2018/0193197 A1* 7/2018 Margulis ................. A61F 11/20

OTHER PUBLICATIONS

Written Opinion for International Application No. PCT/SG2021/050129 mailed May 1, 2021, 5 pages.
The Extended European Search Report for European Patent Application No. 217682381.4, Jul. 7, 2023, 7 Pages.
Office Action for Singapore Patent Application No. 11202250977T, Jul. 10, 2024, 8 Pages.

* cited by examiner

DEVICE FOR INTRODUCING A SEAL INTO AN EAR AND A METHOD FOR REPAIRING A TYMPANIC MEMBRANE

CROSS-REFERENCE TO RELATED APPLICATIONS

The present application is a national phase entry under 35 U.S.C. § 371 of International Application No. PCT/SG2021/050129, filed Mar. 11, 2021, published in English, which claims the benefit of U.S. Provisional Patent Application No. 62/988,590, filed Mar. 12, 2020, which is incorporated herein by reference in its entirety.

FIELD

The present invention relates to a device for introducing a seal into an ear and a method for repairing a tympanic membrane. In embodiments, the present invention relates to device and method for repairing a perforation in a tympanic membrane.

BACKGROUND

It is not uncommon for an eardrum to rupture. Eardrum rupture (Tympanic Membrane Perforation—TMP) can lead to chronic ear discharge due to secondary infection and may affect the hearing level.

In some cases, the eardrum will heal itself over time. However, it is not uncommon for surgery to be necessary. The current procedure for TMP repair requires an open, long and invasive surgery, performed under general anesthesia in the operating room.

Tympanoplasty is a surgical technique to repair a defect in the tympanic membrane with the placement of a graft, either medial or lateral to the tympanic membrane annulus. The goal of this surgical procedure is to close the TMP and improve quality of life. The success of the operation depends on the ability to seal the perforation by a scaffold graft for tympanic membrane regeneration.

Various techniques have been developed and refined, and a number of grafting materials are available. Both the lateral and mainly medial grafting techniques are commonly used in the surgical method.

The surgery often requires an incision made behind the ear to gain access to the tympanic membrane for placement of the graft. The surgery is invasive and can result in prolonged recovery, and complications such as infection, hearing deterioration, and failure to close the TMP. It is desirable therefore to provide a means for performing tympanic membrane repair, while avoiding or reducing the prolonged recovery or risk of infection, or at least to provide a useful alternative to existing methods of repair.

SUMMARY OF INVENTION

Described herein is a device for repair of a region within an ear via a natural orifice, the device comprising:

a body, the body comprising:

- a first port for visibly identifying the region to be sealed, the region being inside the ear; and
- a second port through which a seal can be introduced into the ear through the device.

The region may comprise a perforation of a tympanic membrane of the ear.

The device may be a speculum.

The first port may comprise a magnifying member for magnifying the region inside the ear. The first port may be arranged to maintain visibility of the region during delivery of the seal through the second port.

The second port may comprise an engagement member for engaging a delivery device, the delivery device being for delivering the seal to the region. The engagement member may be configured to engage the delivery device to fix a longitudinal position of the delivery device relative to the second port. The engagement member may comprise a twist lock fixture.

The body tapers distally (i.e. narrows towards its distal end) to facilitate introduction of a distal end of the device into the ear. The device itself may taper from a proximal end, through which a user (e.g. a physician) may view the site within the ear intended to be repaired or otherwise sealed, to a distal end that is inserted into the ear—i.e. taper along its length. This allows a large viewing port while maintaining a small enough distal end to enable it to comfortably insert inside the ear.

The device may include two or more ports, said ports including the first and second ports. At least one of the two or more ports may be configured to receive:

- a surgical device for performing a surgical operation on tissue at the region in the ear;
- a fluid delivery device for delivering fluid to the seal when the seal has been introduced into the ear; and
- fluid and to deliver the fluid to the seal when the seal has been introduced into the ear.

Thus, the surgical instruments, delivery tools and other implements may be inserted through a port of the tympanic membrane repair device to facilitate surgery on the tympanic membrane (or other region inside the ear), while maintaining visibility, of the site being repaired or treated, through the first port.

The surgical operation may comprise removing tissue from around the perforation.

Also disclosed is a method for repairing a tympanic membrane through a natural orifice of an ear, comprising:

- inserting, through a device as described above, an introducer into the ear via the natural orifice, so that the introducer extends at least into a perforation in the tympanic membrane;
- delivering a seal from the introducer to a distal (i.e. medial) side of the tympanic membrane; and
- attaching the seal to the distal side.

The method may further comprise identifying the perforation through a viewing port of the device. The method may further comprise maintaining visibility of the perforation through the viewing port of the device, during the delivering and attaching steps. Where the body tapers distally and introducing the device into the ear may comprise introducing the device until the body abuts the ear.

Introducing the device into the ear may comprise aligning an introducer port with a perforation in a tympanic membrane so that insertion of the introducer causes the introducer to extend through the perforation.

The method may further comprise:

- inserting a surgical instrument through the device; and
- trimming tissue from around the perforation.

The method may further comprise topically anaesthetising an internal region of the ear.

The method may further comprise debriding the tympanic membrane around the perforation.

Inserting the introducer into the ear via the natural orifice, so that the introducer extends at least into a perforation in the tympanic membrane, may comprise:

inserting the introducer to a position proximal on the tympanic membrane;

advancing a guidewire through the perforation; and advancing the introducer along the guidewire and into the perforation.

The method may further comprise retracting the guidewire after advancing the introducer along the guidewire and into the perforation.

Delivering the seal from the introducer may comprise using a pusher to push the seal from within the introducer.

The method may further comprise drawing the seal back against the distal side of the tympanic membrane.

Attaching the seal to the distal side may be performed by adhering the seal to the distal side using at least one of glue, gel or foam.

The seal may be a graft comprising a first body and a second body, the first and second bodies being connected, and wherein delivering the seal from the introducer comprises:

advancing the graft so that the first body is positioned distally of the tympanic membrane;

withdrawing the introducer to a location proximal of the tympanic membrane; and advancing the graft so that the second body so at least part of the tympanic membrane is between the first body and second body.

The first body and the second body may form a double umbrella shape.

The method may further comprise withdrawing the introducer after attaching the seal.

The method may further comprise introducing a device as described above at least partially into the ear, and inserting the introducer into the ear via the natural orifice may then comprise inserting the introducer into the second port of the device.

The body may taper distally and introducing the device into the ear may thus comprise introducing the device until the body abuts the ear. Introducing the device into the ear may also, or instead, comprise aligning the second port with a perforation in a tympanic membrane so that insertion of the introducer causes the introducer to extend through the perforation.

Attaching the seal to the tympanic membrane may comprise:

attaching a suture to the seal; and after the seal has been delivered to the distal side of the tympanic membrane, pulling the suture to bring the seal against the distal side.

Attaching the seal to the tympanic membrane may comprise at least one of:

delivering fluid to the seal through the device to expand the seal to a formed shape; and warming the seal to a temperature sufficient for the seal to expand to the formed shape.

Warming the fluid may involve allowing the fluid to be warmed by the body of the subject or patient, while maintaining a position of the seal.

Also disclosed is a kit comprising:

a device as described above;

a graft for covering the region being repaired; and an introducer for introducing the graft through the device.

The kit may further comprise glue, water and/or other fluids necessary to attach and/or expand the graft once it has been introduced into the ear. The device may be a device as described above. The graft may be a graft as described elsewhere herein, as may be the introducer.

The kit may further comprise a pusher for pushing the seal from within the introducer.

Advantageously, methods described herein, and the devices taught for performing those methods, may enable minimally, or less, invasive repair of tympanic membrane perforation using a delivery device without surgical procedure.

Advantageously, the device introduces the seal through the natural orifice. Consequently, there is no need for invasive surgery.

BRIEF DESCRIPTION OF THE DRAWINGS

Some embodiments of the present invention will now be described, by way of non-limiting example only, with reference to the accompanying drawings in which.

DETAILED DESCRIPTION

Devices disclosed herein enable seals, such as grafts, to be attached to regions within the ear without undesirable surgery. In some embodiments, such as when repairing a perforation in a tympanic membrane, some surgery may be desirable at the perforation to neaten the perforation or to stimulate tissue growth. This minor surgery serves a purpose other than the installation of the seal. With this in mind, the phrase “without surgery” refers to there being no “undesirable surgery”, being surgery that is desirable to avoid, or surgery without which the seal would still be able to be placed in the desired position in the ear and attached to the membrane during installation or placement of the seal.

Figure 1:
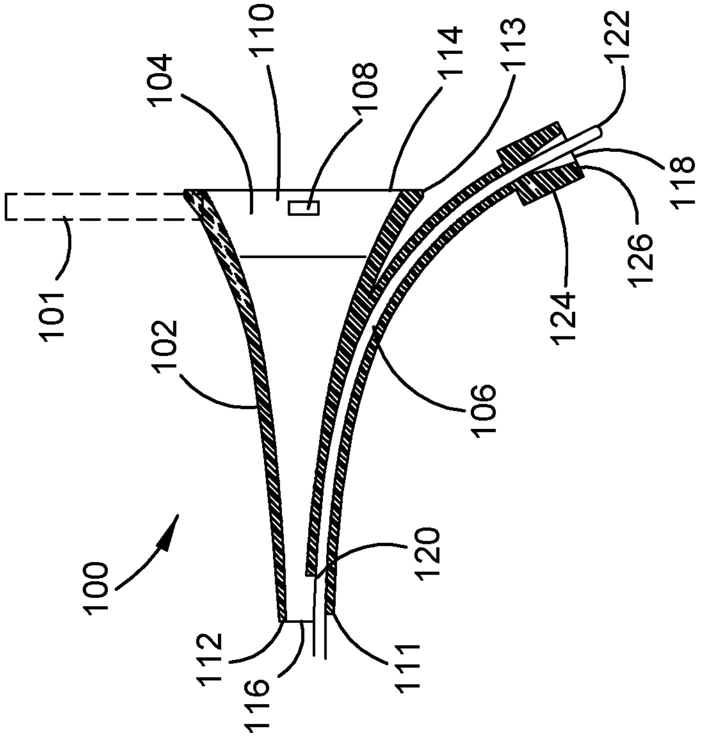
FIG. 1 illustrates an embodiment of a device in accordance with the present teachings, for delivering a seal into the ear.

FIG. 1 shows a device 100 for natural orifice repair of a region within an ear. While the device 100 may be used for various surgical procedures, the description below will explain usage of the device 100 in the context of myringoplasty for illustration purposes. The device 100 can be used to avoid undesirable surgery.

The device 100 broadly comprises a body 102, incorporating a first port 104 and second port 106. The device 100 is, in the present embodiment, a speculum. The device 100 may attach to an otoscope in a known manner—e.g. by a friction connection in which recess 108 engages a lug or protrusion on the otoscope, and the otoscope may carry a magnifying element for magnifying a view through the speculum. The device 100 may therefore be single-use, for discard after separation from the otoscope. In other embodiments, the device 100 may be used by itself or may include a handle to facilitate control of the device 100. A handle (e.g. handle 101, shown in broken lines) or attached otoscope will often be desired to enable the hand controlling the speculum to be distanced from the ear, thereby facilitating access by the other hand to perform TMP repair.

The body 102 is formed from plastic, though it may equally be formed from metal or another suitable material. The body 102 is generally circular in cross-section, though other cross-sections may be desirable for particular applications. The device 100 tapers distally from a proximal end 110 to a distal end 112—in some embodiments, the taper may extend along the full length of the device 100 as shown and, in other embodiments, the taper may only be toward the distal end 111 of the device 100. This taper facilitates introduction of a distal end 111 of the device 100 into the ear. The distal end 111 of the device 100 is therefore sufficiently small to comfortably fit into the ear while the larger, proximal end 113 remains sufficiently large both to comfortably view the site or region—e.g. tympanic membrane—and to easily control the device 100.

In some cases, multiple different tools or substances (e.g. sterilising or antibacterial fluids) are required to be concurrently delivered into the ear. There may therefore be as many ports in the body as needed—e.g. two or more. Presently, the body 102 comprises only the first and second ports 104, 106 respectively. At least one of the ports is configured to receive a surgical device for performing a surgical operation on tissue at the TMP. This operation may result in tissue being removed from the tympanic membrane—e.g. debridement from around the TMP to stimulate tissue growth. The port or ports may be similarly configured to receive a fluid delivery device for delivering fluid to the seal when the seal has been introduced into the ear—e.g. antibacterial fluid—or may instead be configured as the conduit through which fluid flows—in other words to deliver the fluid to the seal when the seal has been introduced into the ear. Since the seal will typically be a graft, that term will be used hereafter for illustration purposes.

The first port 104 is for viewing or visibly identifying the tympanic membrane—or other region to be sealed—inside the ear. The first port 104 therefore includes a pair of apertures 114, 116 in the proximal and distal ends 110, 112 respectively. The apertures 114, 116 are aligned to provide a clear view straight through the device 100.

The first port 104 may be used for insertion of tools in cases where visibility is not necessary. In cases where the seal is being introduced and visibility during insertion is desired, or it is otherwise useful to have visibility while inserting a tool or graft into the ear, the second port 106 facilitates introduction of the seal into the ear through the device 100. Thus, where needed, the first port 104 is arranged to maintain visibility of the tympanic membrane, particularly the TMP, during delivery of the seal through the second port.

To improve visibility and potentially avoid the need for an otoscope or similar device, the first port 104 may comprise a magnifying member for magnifying the tympanic membrane. To further assist, the device 100 may comprise a light source at or towards the distal end 111 to illuminate the external acoustic meatus and/or tympanic membrane.

Figure 2:
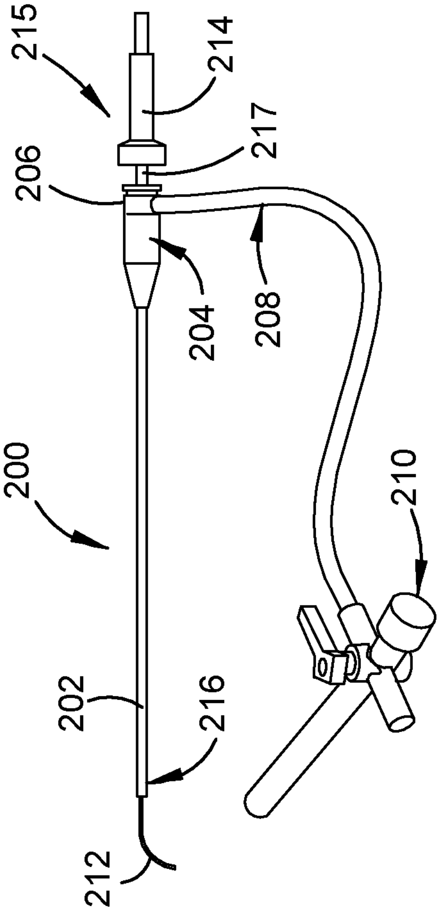
FIG. 2 illustrates an introducer, also known as a delivery tool, for delivering a seal through the device of FIG. 1, into the ear.

The speculum 100 with multiple portal (or port) access may therefore be designed to allow microscopic vision with the delivery device (e.g. device 122 or delivery device 200 of FIG. 2). The delivery device can be inserted directly into the main port (i.e. first port 104) of the speculum 100 or from the side branch (second port 106) of the speculum port access. Both main port 104 of the speculum 100 or the side branch (i.e. port 106) of the speculum 100 allow the introducer tube 122 to be secured to the port access (i.e. proximal end of the port) of the speculum 100 by any suitable means such as, with reference to port 106, a twist lock shape fixture so it does not move during the delivery of the graft. First the first port 104, the device may secure to recess 108 to affect a friction fit.

The second port 106 extends from a proximal entry point 118 to a distal exit point 120, without obscuring the view through the first port 104. The exit point 120 may be within the first port 104, may be next to the distal end of the first port 104 or may be shared with the distal end of the first port 104 (i.e. aperture 116). The second port 106 may be curved as shown, to conform with a curvature of the body, or may be straight or another shape as desired.

The second port 106 comprises an engagement member 124 for engaging a delivery device 122. The delivery device 122 is used for delivering a seal (e.g. a graft) to the TMP. However, the delivery device 122 may be a device configured, in a known manner, to instead introduce a surgical tool into the ear, to deliver fluid into the ear or perform any of a number of other procedures for which controlled access to the area within an ear is desired.

The engagement member may be located at any location on or within the second port—note: in this context, the second port is effectively a conduit extending through the body 102, and the first port 104 will be given a similar construction. Presently, the engagement member 124 is located at the proximal end 126 of the second port 106. The engagement member 124 is configured to engage the delivery device 122 to fix a longitudinal position of the delivery device relative to the second port—fixing the longitudinal position means, with respect to longitudinal axis X, preventing further movement of the delivery device 122 both proximally and distally. In the embodiment shown, the engagement member 124 comprises a twist lock fixture. The twist lock fixture engages a corresponding twist lock fixture on the delivery device 122. Other fittings for substituting for the twist lock fixture may include luer fittings and the like.

Notably, the term "port" as used herein includes refers to conduits in the device 100 through which visibility of the inside of the ear can be gained, in the case of the first port 104, and through which instruments can be inserted into the ear, in the case of the second port 106.

The delivery device 122 may take any desired form. As shown in FIG. 2, the delivery device 200 includes a catheter (hereinafter introducer 202) extending distally from a catheter hub 204, a valve hub 206 inserted into the rear of the catheter hub 204 and from which a side tube 208 extends to a three-way stop cock 210. A guidewire 212 extends through the catheter from a proximal grip 214 located proximally of a proximal end of the valve hub 206, to a location distal of the distal tip 216 of the introducer 202. The grip 214 forms part of the pusher 215, that further comprises a hollow tube 217 extending within the catheter 202, for pushing the graft from within the introducer into position on the tympanic membrane. The hollow tube 217 presently has a tapered distal tip.

Figure 5:
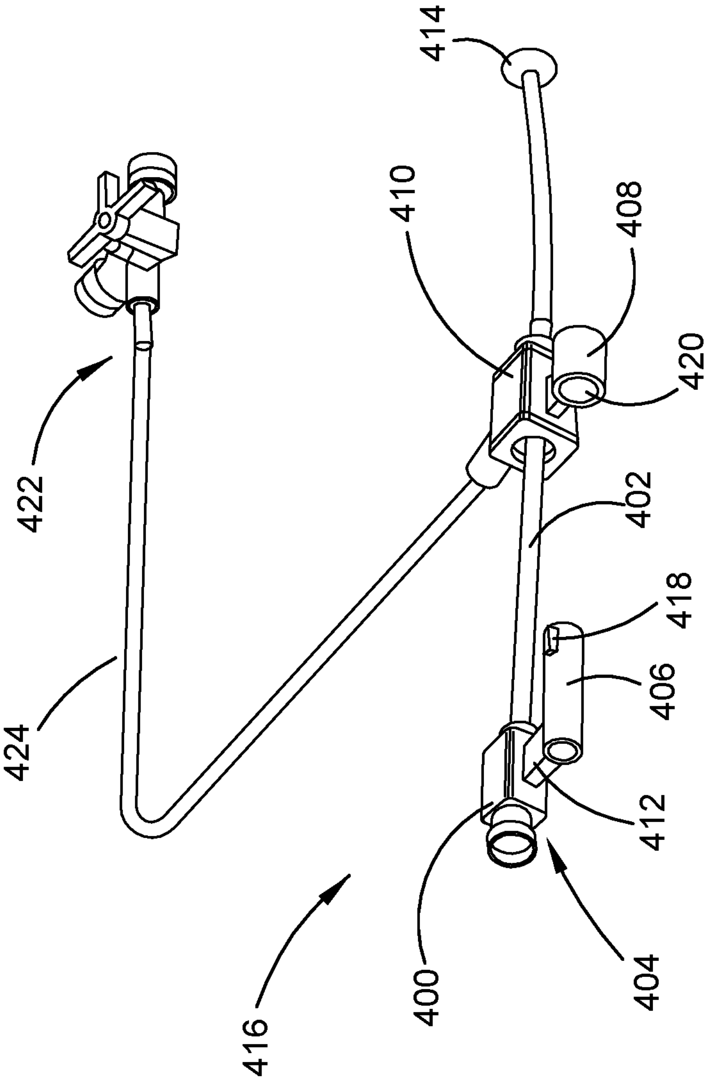
FIG. 5 shows the introducer and pusher component of FIG. 4, assembled together with a hub and other components to form device for placement of a graft through a perforation in a tympanic membrane.
Figure 4:
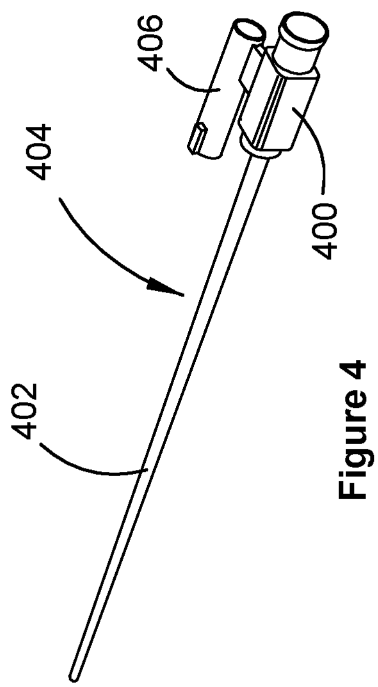
FIG. 4 shows an alternative embodiment of an introducer and pusher.

FIG. 4 shows another, partial embodiment of the delivery device more clearly illustrating the grip 400 and pusher 402 forming a single component 404. Notably, the component 400 also comprises a guide 406. The guide 406 guides movement of the pusher 402 to serve one or more of a variety of purposes. The guide 406 is received in a corresponding guide 408 of a hub 410 (e.g. two-way or three-way port) as shown in FIG. 5. An arm 412 serves to space the guide 406 from the grip 400. During movement of the pusher 402 into and through the hub 410 during deployment of a graft 414, the guide 406 contacts—presently, is received in—the corresponding guide 408. On reaching the most distal position of the pusher 402, the guide 406 and corresponding guide 408 come into abutment and prevent further advancement of the pusher 402. This indicates to a user of the device 416 that the graft 414 has been deployed.

The guide 406 may also ensure proper orientation of the pusher or a guidewire (not shown) extending therethrough for fine control of the position of the graft 414 on deployment. To that end, guide 406 comprises a key 418 to fit in a keyed aperture 420 of the corresponding guide 408—the key 418 and aperture 420 may fit together in one unique orientation only, so that the orientation of the pusher in the ear is known.

Figure 6:
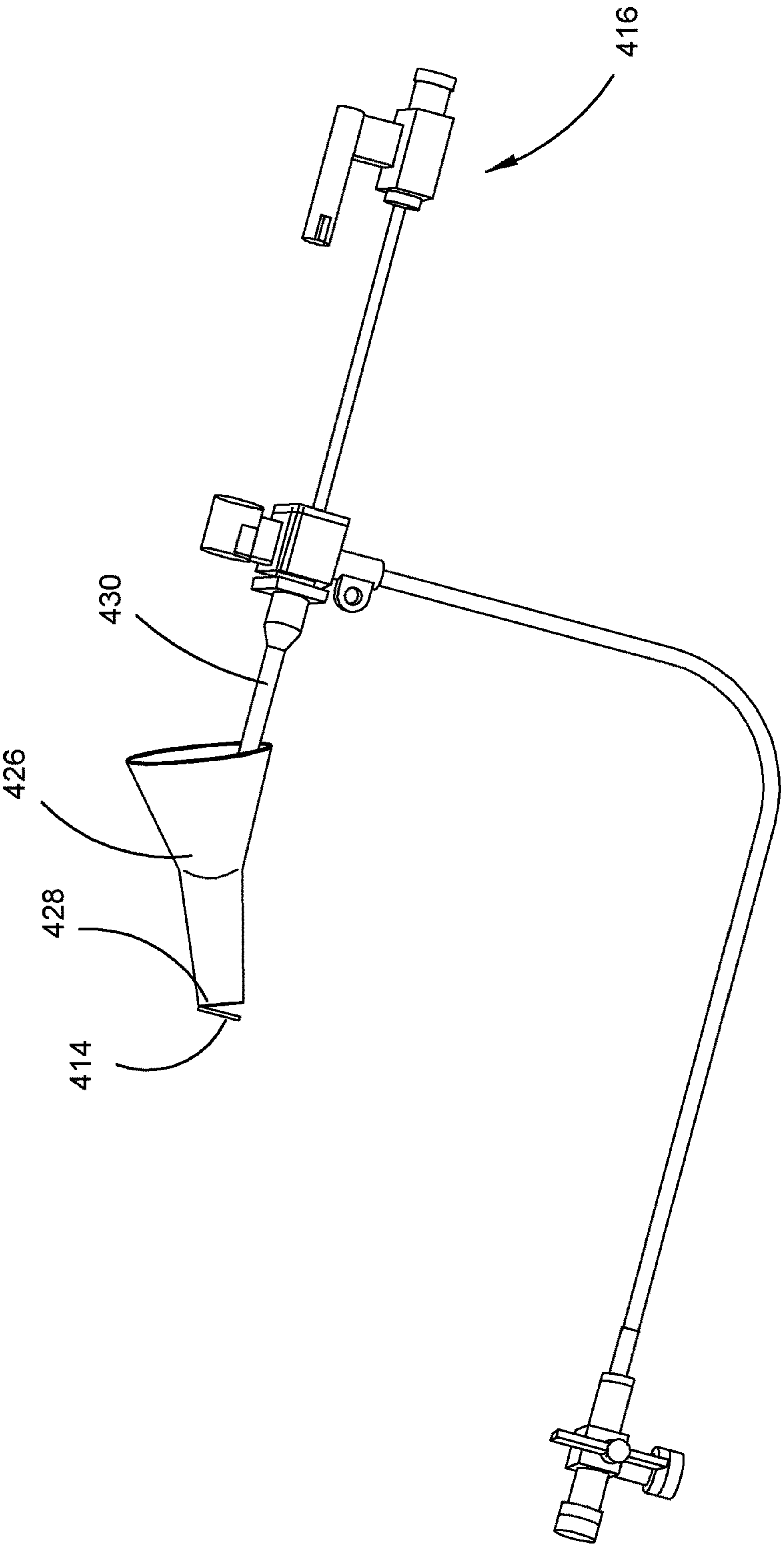
FIG. 6 shows the device of FIG. 5 with the introducer extending into an ear for placement of a graft.

Presently, the device 416 includes a stop cock 422 and side tube 424 for introducing fluid, adhesive, cell growth medium or other substance after placement of the graft 414. The device 416 is also shown in FIG. 6, with introducer (tube 430) extending into an ear 426, to position a graft 414 at a distal side of the tympanic membrane 428. When in use with a two-bodied graft (i.e. a graft comprising two bodies that are connected), the intention is to capture the tympanic membrane between the bodies. This does not mean the full tympanic membrane is captured but instead means that a sufficient amount of the membrane is captured so the perforation is between the two bodies of the graft. To achieve this, the introducer is advanced through the device—e.g. device shown in FIG. 1—until the tip of the introducer is distal of the tympanic membrane. One of the two bodies of the graft is then delivered from the introducer (e.g. using the pusher) to the distal side of the membrane. The introducer is then retracted or withdrawn slightly so that the tip of the introducer is now proximal of the tympanic membrane. The second body is then delivered. As a result, the two bodies will come together against opposite sides of the tympanic membrane, with the perforation therebetween. The two bodies can be adhered to the membrane—e.g. by addition of adhesive after placement, or by pre-loading with adhesive the side of each body that contacts the membrane—or may already be sufficiently resilient to hold themselves against the membrane without further adhesion. The graft may also be sutured to the membrane or attached by any other suitable method or properties of the graft.

The device, introducer, pusher, guidewire, graft and all other parts of the system used for tympanoplasty in accordance with present teachings can have any dimensions suitable for a particular patient or subject. For example, the length of the introducer sheath (i.e. catheter 202) may be 5, 7, 9, 11 or 13 cm. The introducer or sheath French sizes may be 5, 6, 7, 8, 9, 10, 11, 12 or 13. The speculum distal outer diameter size may be 4 mm to 13 mm with length of 3 mm to 6 mm. The graft will usually be anywhere between 2 mm to 15 mm in diameter and may be, as discussed below, trimmed to size. The present teachings will, however, apply to speculums and grafts of dimensions falling outside these ranges.

The graft may be biodegradable. Moreover, the graft may be made of a single material, such as a hydrogel, a biodegradable polymer or esterified hyaluronic acid, or a combination of materials. The graft could be made of part human tissue extracted from different parts of the body, naturally occurring polymer and hydrogel, synthetic polymer, chemically modified natural polymer (e.g. methacrylated hyaluronic acid, methacrylated collagen and methacrylated gelatin), modified synthetic polymer and modified natural polymer and is not limited to these examples. With the exception of materials explicitly disclaimed, the graft may be formed from any material suitable for the application of the graft and, in particular, the repair of a tympanic membrane.

The structure or shape of the graft may vary, depending on the size of the rupture in the membrane. For example, the graft may be a single disc, thin-film synthetic graft. In other embodiments, the graft may comprise two bodies, where one body is pushed through the rupture in the membrane and the other body remains on an outer side of the membrane (i.e. closer to the natural orifice). The bodies can be connected—either directly or via a tube or other bridging member—through the aperture so as to sandwich the membrane therebetween. Such a two-bodied structure may comprise a disc film or a double "umbrella" shape connected with an annular tube (bridging portion).

The graft may, as mentioned above, be a combination of materials. For example, one body or disc can be esterified hyaluronic acid, connected with a biodegradable tube to the other body or disc which is made from a biodegradable polymer. The different material can be fused into shape by sutures, 3D printing solvents, casting, mold-polymerization (thermal and photo polymerization) or heat bonding, thermal and light-activated polymerization and other methods.

The unique shape of the two body graft allows the graft to be secured and to patch the perforation in the tympanic membrane without the need of additional adhesives.

The deployment of an esterified hyaluronic acid film secured with suture or its equivalent, or by sandwiching the membrane between two bodies, may be deployed by folding it on a pusher tube and pushing it through an introducer that extends through the natural orifice and is fixated on a trimmed perforated tympanic membrane.

The esterified hyaluronic acid (HA esters) may use one or more of aliphatic, arylaliphatic, cycloaliphatic, aromatic, cyclic and heterocyclic alcohols. The esterification percentage may vary according to the type and length of alcohol used, from 50 to 100%. The graft may be formed with perforations or micro-perforations to allow permeability—this facilitates drainage of exudate from the perforation—e.g. at the surgical site.

In the case of graft comprising hydrogels, the graft may comprise, but are not limited to, any appropriate materials such as acrylate monomers, polyvinyl alcohol, sodium polyacrylate, acrylate polymers or copolymers, agarose, methylcellulose, hyaluronan, collagen or any combination thereof. Non-limiting examples of chemical compounds suitable for use in the formation of the graft include Gelatin Methacryloyl (GelMA), Methacrylated Collagen, acrylamide, Trimethylolpropane ethoxylate triacrylate, and photoinitiators, such as but not limited to 2,4,6-trimethylbenzoyl-diphenylphosphine oxide (TPO) nanoparticles or 2-Hydroxy-4'-(2-hydroxyethoxy)-2-methylpropiophenone or any other suitable chemical compounds or combination of compounds. Other grafts may be used with the delivery device to seal the perforation, examples of which include a collagen membrane, allografts, mucograft, dermal membrane, pericardium membrane, Albumin membrane, cellulose membrane, small intestine submucosa membrane, chitosan membrane, hyaluronic membrane, and gelatin membrane. Notably, the size and shape of the graft are not specified. The graft may have a size and shape appropriate for its use. For example, the graft, or each body of a two-body graft, may be circular, square, or a custom shape to fit the membrane or perforation. Moreover, the two bodies of a two-body graft need not have the same shape. Similarly, the graft may cover the full membrane, only just cover the perforation, or have any other size as needed—e.g. to extend past the membrane to enable anchoring on another part of the ear or inner ear.

The hydrogel may be at least partially coated by a material configured to induce cell growth on the graft—e.g., collagen or other biocompatible material. This enables controlled promoting of cell growth—in contrast, injecting cell growth material into the middle ear may cause uncontrolled, excessive growth of epithelial cells within the middle year.

There are also a number of biodegradable polymers derived from natural sources such as modified polysaccharides (cellulose, chitin, chitosan, dextran) or modified proteins (fibrin, casein). For example, PLGA 7525 can be used as reinforcement strips and covered by umbrella shape graft film PLGA 50/50.

Where the graft comprises biodegradable polymers, the graft may comprise, but are not limited to, one or more of polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, and polyphosphazene, and copolymers, terpolymers and combinations and mixtures thereof. There are also a number of biodegradable polymers derived from natural sources such as modified polysaccharides (cellulose, chitin, chitosan, dextran) or modified proteins (fibrin, casein). These polymers may be used for film making the graft material via solution coating or other processes. The graft may also comprise one or more reinforcement strips—e.g. extending radially from the bridging portion or otherwise across a surface of the graft. The reinforcement strip or strips may be on the surface of the graft facing the membrane, and/or the opposite surface of the graft—for two body grafts, the strip or strips may be on one or both bodies, as needed.

After placement, step 326 may involve delivering fluid by the introducer tube, to enlarge the biodegradable graft by absorption of the fluid. The composition of the hydrogel may be configured to ensure a controlled enlargement. For example, enlargement may be directed primarily along the longitudinal axis of the graft—the longitudinal axis extends into the ear, roughly normal to the plane of the tympanic membrane. According to some embodiments, the biodegradable graft comprises a material configured to prevent axial enlargement—axial enlargement is enlargement in a direction generally radially from the longitudinal axis. In the two-body graft example discussed above, the longitudinal axis would be an axis extending through the connection between the two bodies, whereas the axial direction extends perpendicular to the longitudinal axis or generally in the respective planes of the two bodies. In this regard, by enlarging the two bodies in the longitudinal direction, the two bodies close the gap therebetween and sandwich the membrane in that gap between the bodies.

Steps 324 and 326 may both be used during attachment of the seal (step 306) or only one of steps 324 and 326 may be used. Where step 324 is used, the biodegradable graft may include a biological adhesive (glue and/or foam) or that adhesive may be applied after placement of the graft. As a result, the risk of detachment of the graft, and thus graft failure due to graft migration, is significantly decreased.

Figure 3:
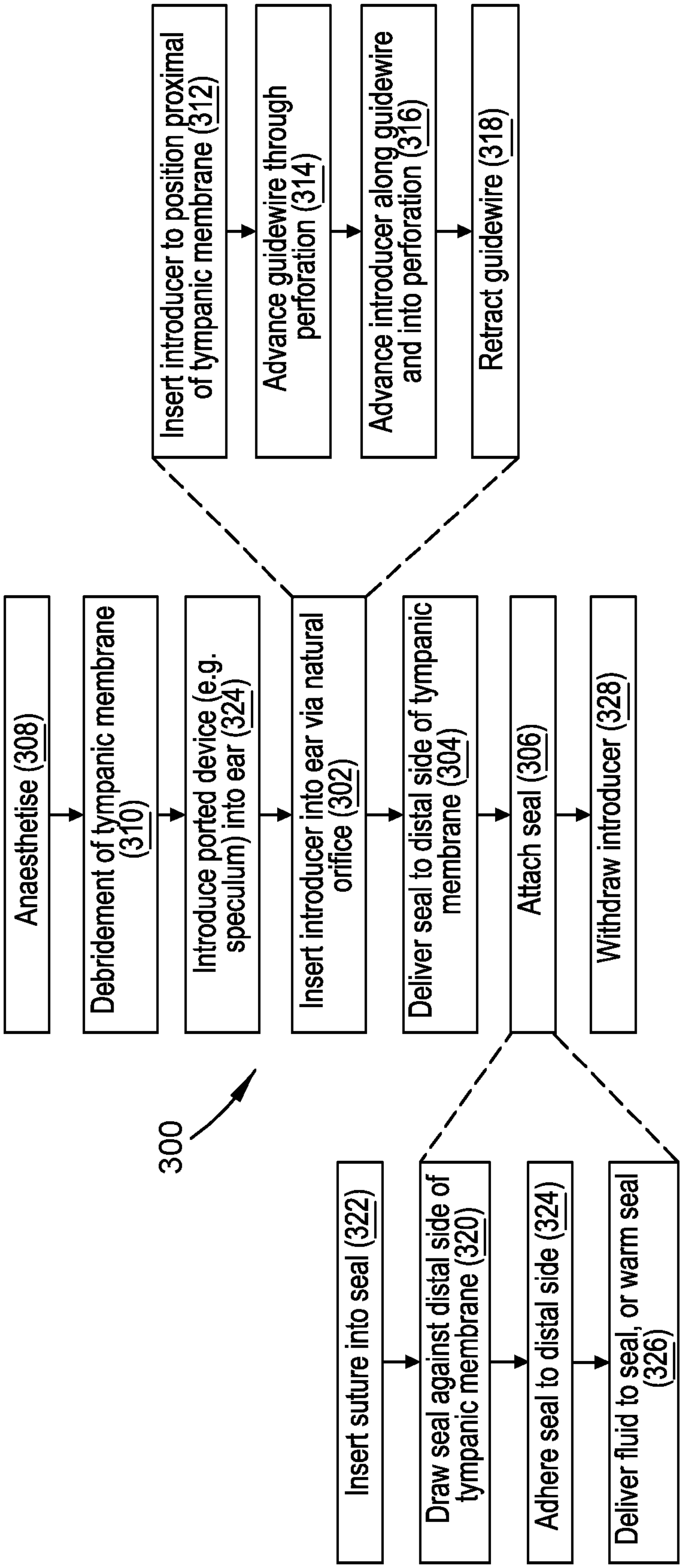
FIG. 3 is a flowchart of a method for repairing a tympanic membrane, in accordance with present teachings.

The delivery device 200 and speculum 100 can thus be used in operations for the repair of a tympanic membrane. In embodiments in accordance with present teachings, a method 300 (see FIG. 3) for repairing a tympanic membrane through a natural orifice of an ear comprises (step 302) inserting an introducer, through a device such as that described with reference FIGS. 1 and 2, into the ear via the natural orifice, so that the introducer extends at least into a perforation in the tympanic membrane, (step 304) delivering a seal from the introducer to a distal side of the tympanic membrane, and (step 306) attaching the seal to the distal side.

In general, for patient comfort, in advance of performing step 302, anaesthetic will be applied (step 308). The anaesthetic may be topical, and applied to an internal region of the ear, or may be general if desired. Usually, however, procedures performed in accordance with present teachings will not require general anaesthetic.

Anaesthetic may be particularly desired where debridement is required around the perforation, to either stimulate new tissue growth or to remove damaged tissue (step 310).

While various methods for properly positioning the introducer (step 302) may be used as a particular procedure or circumstances require, it is envisaged that this will generally involve (step 312) inserting the introducer to a position proximal on the tympanic membrane, (step 314) advancing a guidewire through the perforation, and (step 316) advancing the introducer along the guidewire and into the perforation. Thus, step 312 aligns the second port 106 (particularly the distal end 120 thereof) with the perforation. The insertion of the guidewire (step 314) ensures the introducer follows the correct path. This is particularly important where, for example, the perforation is around the same size as the introducer, to ensure the introducer does not force a tear in the tympanic membrane around the perforation. Step 316 then ensures the graft can be delivered to the back (distal side) of the tympanic membrane.

Per step 318, the guidewire will typically be removed after the introducer has been advanced along the guidewire and into the perforation. In some embodiments, however, the guidewire may be used to guide a graft or other implement behind the tympanic membrane.

Step 304 may be performed in a variety of ways depending on the nature of the graft. The graft may comprise an esterified hyaluronic acid film or any other desirable material. The deployment of an esterified hyaluronic acid film (e.g. which may be secured with suture as discussed below) or its equivalent may be required for the graft to be folded on the pusher or pusher tube and to enable it to easily be pushed through within the introducer, through the natural orifice of the ear, and to be fixated on a trimmed (e.g. debrided) perforated tympanic membrane using the same delivery device as that through which debridement occurred.

In the embodiment shown in FIG. 2, the graft is preloaded with a suture. The graft may also be trimmed to the required size and/or shape to cover the perforated hole (if trimming is needed). After the introducer is aligned with the tympanic perforation, the guidewire is withdrawn and the proximal end of the suture is inserted through the distal end of the pusher (hollow tube 217) until the proximal end of the suture extends through the grip 214 (which is also hollow and thus a continuation of the hollow tube 217). The surgeon then pulls the proximal end of the suture to bring the graft against the distal tip of the pusher. The graft is then inserted through the introducer 202 from the proximal end (at hub 204). The graft is delivered from the introducer using the pusher to push the seal from the introducer.

Thus, the biodegradable graft is pulled against the tip of the pusher by the securing suture as discussed below, and is pushed out from the introducer tubular section by the pusher after retrieving the guide wire after the tip of the introducer is positioned through the perforation in the tympanic membrane. In other embodiments, the graft may be small enough to be inserted through the pusher from the proximal end of the pusher, until it emerges from the distal end of the pusher. The graft may similarly be then brought against the distal end or tip of the pusher by pulling the proximal end of the suture.

After the graft has been delivered behind the tympanic membrane, it is then drawn (e.g. pulled) back against the distal side of the tympanic membrane (step 320)—in this sense, being "against" the membrane includes being juxtaposed to the membrane. To draw the graft against the distal side of the tympanic membrane, a suture is attached (i.e. inserted or sutured) to the graft (step 322) as mentioned above. The suture extends through the introducer to a position proximal of the proximal end 118 of the second port 106. This enables the suture to be grasped by a physician and pulled to bring the graft against the tympanic membrane. Thus, in cases where a biodegradable graft, suture, introducer and pusher are used, the biodegradable graft is fastened and/or juxtaposed to the tympanic membrane by, for example, pushing the suture, that is attached to the biodegradable graft that is itself against the tip of the pusher, out of the introducer tube tip positioned in the middle ear through the perforated hole and pulling back the biodegradable graft to the medial (e.g. distal) side of the tympanic membrane like an opened "umbrella" (e.g. by pulling the suture once the graft has expanded), such that the biodegradable graft at least partially covers the perforation in the tympanic membrane.

In other embodiments, a grasping tool may be used to pull the suture so that the suture need not extend proximally from the second port 106, or may be used to pull the graft directly, thereby avoiding the need for a suture. If the securing suture comes loose, the graft can still be delivered via an endoscopic grasper with a section of the graft that allows it to be grasped. The biodegradable graft is then adhered to the medial side of the tympanic membrane using a biological glue or other mechanism (e.g. gel) which may be injected through the introducer tube 202 via the side tube 208 of the delivery device 200 with multiple valves (around stop cock 210) for attachment. Once the graft is "fastened" to the medial side of the tympanic membrane, the secured suture can be cut off.

In yet further embodiments, a self-expanding graft may be used that will bring itself into sufficiently close proximity to the tympanic membrane to facilitate sealing and healing. Alternative forms of graft may be used that facilitate fixation without the use of adhesives and the like.

Once against the distal side of the tympanic membrane, the graft may be attached thereto by adhesion (step 324). Adhesion may involve using at least one of glue, gel or foam as the adhesive. The introducer 202 may include a UV light catheter for curing the glue or hydrogel inserted through the introducer tube if UV curable glue or material is used for fastening the tympanic membrane graft. In addition, or alternatively, attaching the graft to the distal side of the tympanic membrane may involve delivering fluid to the seal through the device to expand the graft to a formed shape (step 326). The fluid may be injected through the introducer tube to contact the graft. The fluid may either be absorbed by the graft to increase its coverage dimension through the natural orifice within the middle ear—the graft therefore enlarges so that it covers the perforation in the tympanic membrane—or may warm the graft to facilitate its expansion or to activate glue on a surface of the graft. In other embodiments, the graft is a biodegradable graft configured or formed from a shape-memory material. The shape-memory material may be configured to expand as a result of being exposed to body-temperature or as a result of being exposed to fluids at ≤40° C. The graft material could also be highly absorbent material such that the amount of fluid absorption allows it to expand to up to twice its original dimension within 45 minutes. The expansion can be tailored according to the final need. In many cases the graft, which may be a biodegradable graft, may undergo an expansion step before a fixation step to attach the graft to the tympanic membrane. The biodegradable graft may be secured in multiple steps, for example, firstly by being expanded by fluid and secondly by being fixated by the injection of an adhesive as discussed above. Growth factor agent can also be introduced through the introducer to increase epithelial cell growth for recovery of the tympanic membrane when fused with the graft.

After attachment of the graft, the introducer is withdrawn from the ear (step 328). In cases where a suture is used to draw the graft against the distal side of the tympanic membrane, the suture may be cut and removed either before or after withdrawal of the introducer.

To controllably insert the introducer, the device 100 of FIG. 1 may first be inserted (step 330) either before or after anaesthetization (step 308). The physician therefore views the tympanic membrane through the first port 104, and introduces the introducer through the second port 106. The device 100 may be inserted until the body 102 abuts the ear such that maintaining comfortable pressure of the device 100 on the ear will ensure the device 100 remains in fixed position relative to the tympanic membrane. Due to the tight control that can be afforded using the device 100, the distal end of the second port may be aligned with the perforation so that no guidewire is required for the introducer to extend through the perforation.

While the broad form of method 300, namely steps 302, 304, 306 may be sufficient to repair a perforation in a tympanic membrane, the method will likely, in practice, involve:

- Topical anesthesia, using an anaesthetic such as xylocaine 10% is applied on the ear through the ear canal (natural orifice).
- Debridement of tympanic perforation for example by utilizing a Rosen needle.
- Insertion of the introducer tube 202 from the outer ear through a multiple port speculum (device 100) or direct insert without speculum just before the perforation of the tympanic membrane. The introducer 202 can be secured with the speculum 100 at the main portal access 104 or the side portal access 106.
- Insertion of the guidewire 212 through the introducer 202 from a proximal end (at or proximally of grip 214) to the tapered distal end 216 into the perforated hole in the tympanic membrane for positioning the tip of the introducer 202 to deploy the graft.
- Once the guidewire 212 is passed through the perforated hole on the membrane: pushing the distal end of the introducer 202 through the perforation. Care must be taken to trim the perforation to be larger than the distal tip of the introducer.
- Retracting the guidewire 212 since the introducer tip has passed through the perforated hole.
- Trimming the biodegradable graft to size to cover the perforated hole in the medial side and mounting the graft on the pusher. Pass a suture through the graft and pull it back to secure the suture and centralize the biodegradable graft.

Inserting the pusher with the mounted biodegradable graft into the proximal end 206 of the introducer tube 202, and pushing the graft out of the introducer tube distal end 216 into the middle ear. The graft will open up slightly and can then be pulled back against the medial (i.e. distal) side of the tympanic membrane with the pusher supporting the graft. The graft preferably includes a suture string as discussed above, or other element, configured to hold and or steer the graft during the procedure. The biodegradable graft is thus introduced through the introducer distal end into the middle ear with a pusher or grasper and retracted back medially to the tympanic membrane with the pusher or grasper supporting it after releasing the graft.

Expanding the graft by applying a fluid, e.g. heated distilled water onto the graft for shape memory graft. In any case, the method for delivery allows the attaching (i.e. fastening and/or juxtaposing) of the graft to the medial side of the tympanic membrane such that the graft covers the perforation in the tympanic membrane.

Depending on the shape and graft type: securing the graft with biological glue and/or gel and/or foam at the lateral side of the tympanic membrane—the glue and/or gel and/or foam may also be delivered through the introducer side tube. During this step, the physician may pull the string attached to the graft against the pusher tip, thereby juxtaposing the graft to the eardrum supported by the pusher tip if the graft is shaped as a flat disc.

After the glue has adhered the graft to the eardrum: withdrawing the pusher and introducer tube 202 per step 328.

Cutting the suture holding the graft.

The method 300 may therefore be used for repairing a perforation in a tympanic membrane through the natural orifice with a biocompatible graft using a delivery device. This avoids the need for undesirable surgery and, in many cases, will avoid the need for surgery altogether with the exception of occasional debridement to stimulate new tissue growth.

In accordance with the description above, the present disclosure presents a delivery device and methods for repairing a perforation in a tympanic membrane. The device will generally be in the form of a speculum with multiple portal (i.e. port) access and will, in the performance of tympanoplasty or myringoplasty, employ an introducer member such as a distal tapered end hollow tube with a pusher from the proximal end, a guide wire inserted through the proximal end of introducer to guide the introducer into the perforation hole through the speculum, and a biodegradable graft inserted into the hollow tube from proximal end through the tympanic membrane perforation in the distal end to a middle ear medially to the tympanic membrane.

The device and methods, disclosed herein, obviate the need for invasive incisions. Thus, procedures performed using the device need not be performed in a surgical theater associated with myringoplasty, and thus the repair can be performed in an equipped clinic or mobile clinic.

The method and devices can allow a tympanic membrane repair procedure to be completed in less than 45 minutes and require only a topical anesthesia as opposed to the general anesthesia associated with myringoplasty.

The minimally invasive nature of this procedure will result in a painless wound, promote recovery and avoid side effects due to surgical procedures compared to myringoplasty.

Many modifications will be apparent to those skilled in the art without departing from the scope of the present invention In this specification and the claims that follow, unless stated otherwise, the word "comprise" and its variations, such as "comprises" and "comprising", imply the inclusion of a stated integer, step, or group of integers or steps, but not the exclusion of any other integer or step or group of integers or steps.

References in this specification to any prior publication, information derived from any said prior publication, or any known matter are not and should not be taken as an acknowledgement, admission or suggestion that said prior publication, or any information derived from this prior publication or known matter forms part of the common general knowledge in the field of endeavour to which the specification relates.

The invention claimed is:

1. A system for repair of a region within a natural orifice of an ear, comprising:

a device for repair of a region within the natural orifice of the ear, comprising: a body that tapers distally to facilitate introduction of a distal end of the device into the ear, the body comprising:

a first port comprising a magnifying member, the first port being for visibly identifying the region to be sealed and being arranged to maintain visibility of the region during delivery of a seal through a second port, the region being inside the ear, wherein the magnifying member magnifies the visibly identified region inside the ear and wherein the second port is a port through which the seal can be introduced into the ear through the device;

the seal for covering the region being sealed; and an introducer for introducing the seal through the device, into the ear via the natural orifice, so that the introducer extends at least into a perforation in the region.

2. The system of claim 1, wherein the perforation is a perforation of a tympanic membrane of the ear.

3. The system of claim 1, wherein the device is a speculum.

4. The system of claim 1, wherein the second port comprises an engagement member for engaging a delivery device, the delivery device being configured to deliver the seal to the region.

5. The system of claim 4, wherein the engagement member is configured to engage the delivery device to fix a longitudinal position of the delivery device relative to the second port.

6. The system of claim 4, wherein the engagement member comprises a twist lock fixture.

7. The system of claim 1, wherein the device comprises two or more ports, including the first port and the second port, and wherein at least one of the two or more ports is configured to receive:

a surgical device for performing a surgical operation on tissue at the region inside the ear;

a fluid delivery device for delivering fluid to the seal when the seal has been introduced into the ear; and the fluid, and wherein at least one of the two or more ports is configured to deliver the fluid to the seal when the seal has been introduced into the ear.

8. A method for repairing a tympanic membrane through a natural orifice of an ear, comprising:

inserting, through a device comprising a body that tapers distally to facilitate introduction of a distal end of the device, into the ear, the body comprising a first port comprising a magnifying member, the first port being for visibly identifying a region within the ear via the natural orifice to be sealed and being arranged to maintain visibility of the region during delivery of a seal through a second port, the region being inside the ear, wherein the magnifying member magnifies the visibly identified region inside the ear and wherein the second port is a port through which the seal can be introduced into the ear through the device, an introducer into the ear via the natural orifice, so that the introducer extends at least into a perforation in the tympanic membrane;

delivering the seal from the introducer to a distal side of the tympanic membrane; and attaching the seal to the distal side.

9. The method of claim 8, wherein the seal is a graft comprising a first body and a second body, the first and second bodies being connected, and wherein delivering the seal from the introducer comprises:

advancing the graft so that the first body is positioned distally of the tympanic membrane;

withdrawing the introducer to a location proximal of the tympanic membrane; and advancing the graft so that at least part of the tympanic membrane is between the first body and second body.

10. The method of claim 9, wherein the first body and the second body form a double umbrella shape.

11. The method of claim 8, wherein attaching the seal to the tympanic membrane comprises:

attaching a suture to the seal; and after the seal has been delivered to the distal side of the tympanic membrane, pulling the suture to bring the seal against the distal side.

12. The method of claim 8, wherein attaching the seal to the tympanic membrane comprises at least one of:

delivering fluid to the seal through the device to expand the seal to a formed shape; and warming the seal to a temperature sufficient for the seal to expand to the formed shape.

13. A kit comprising:

a device comprising a body that tapers distally to facilitate introduction of a distal end of the device into an ear, the body comprising:

a first port comprising a magnifying member, the first port being for visibly identifying a region within the ear via a natural orifice to be sealed and being arranged to maintain visibility of the region during delivery of a seal through a second port, the region being inside the ear, wherein the magnifying member magnifies the visibly identified region inside the ear and wherein the second port is a port through which the seal can be introduced into the ear through the device;

a graft for covering the region being repaired; and an introducer for introducing the graft through the device.

* * * * *